United States Patent [19]

Ishikawa et al.

[11] Patent Number: 4,809,703

[45] Date of Patent: Mar. 7, 1989

[54] ULTRASONIC DOPPLER BLOOD FLOW METER

[75] Inventors: Shizuo Ishikawa, Kanagawa; Kageyoshi Katakura, Tokyo; Toshio Ogawa, Tokyo, all of Japan

[73] Assignee: Hitachi Medical Corp., Tokyo, Japan

[21] Appl. No.: 101,444

[22] Filed: Sep. 28, 1987

[30] Foreign Application Priority Data

Sep. 29, 1986 [JP] Japan .................. 61-230887

[51] Int. Cl.$^4$ .............................................. A61B 10/00
[52] U.S. Cl. .............................................. 128/661.08
[58] Field of Search ............... 128/663; 73/861.25, 73/861.31, 861.27

[56] References Cited

U.S. PATENT DOCUMENTS

4,583,409  4/1986  Lannuzel et al. ............... 73/861.25
4,671,294  6/1987  Magnin et al. .................. 73/861.25
4,680,739  7/1987  Lannuzel ......................... 128/663

Primary Examiner—Francis J. Jaworski
Assistant Examiner—George Manuel
Attorney, Agent, or Firm—Antonelli, Terry & Wands

[57] ABSTRACT

An ultrasonic Doppler blood flow meter comprises a transmit-receive transducer transmitting ultrasonic wave toward and into a living body and receiving an echo signal, quadrature detectors detecting a real (R) component and an imaginary (I) component of the receiving echo signal respectively, A/D converters converting analog output signals of the quadrature detectors into digital signals respectively, a converter subjecting the R and I components to quadrature transformation to generate output signals representing the absolute value and phase angle ($\theta$) respectively of the received echo signal, and a signal processing circuit calculating the mean value of the differences ($\Delta\theta_i = \theta_i - \theta_{i-1}$) between the phase angles ($\theta_i$) and their preceding ones ($\theta_{i-1}$) detected when the ultrasonic wave is transmitted and the echo signal is received a predetermined number of times. In the signal processing circuit, the phase angle differences ($\Delta\theta$) are each resolved into an X-axis component (cos $\Delta\theta$) and a Y-axis component (sin$\Delta\theta$), and, after calculation of the mean values $\overline{X}$ and $\overline{Y}$ of n consecutive X-axis and Y-axis components respectively, the mean Doppler shift phase angle $\Delta\theta = \tan^{-1}(\overline{Y}/\overline{X})$ is calculated on the basis of the calculated mean values $\overline{X}$ and $\overline{Y}$.

6 Claims, 6 Drawing Sheets

|   | $\Delta\theta_i$ |
|---|---|
| a | 170 |
| b | 175 |
| c | -175 |
| d | -170 |
| e' MEAN VALUE | 0° |

FIG. 3C

|   | $\Delta\theta_i$ | |
|---|---|---|
|   | $X(\cos\Delta\theta_i)$ | $Y(\sin\Delta\theta_i)$ |
| a | -0.985 | 0.174 |
| b | -0.996 | 0.087 |
| c | -0.996 | -0.087 |
| d | -0.985 | -0.174 |
| e MEAN VALUE | -0.991 ($\overline{X}$) | 0.0 ($\overline{Y}$) |
| $\overline{\Delta\theta}=\tan^{-1}\frac{\overline{Y}}{\overline{X}}$ | 180° | |

ULTRASONIC DOPPLER BLOOD FLOW METER

BACKGROUND OF THE INVENTION

This invention relates to an ultrasonic Doppler blood flow meter, and more particularly to a blood flow meter of the type described above in which the manner of measurement of the frequency of echoes of ultrasonic wave reflected from a living body is improved.

Prior art, ultrasonic Doppler blood flow meters are disclosed in, for example, C. Kasai et al, "Real-Time Two-Dimensional Blood Flow Imaging Using an Autocorrelation Technique" IEEE Transactions on Sonics and Ultrasonics, Vol. SU-32, No. 3, May 1985, pp. 458–464 and D. W. Baker, "Pulsed Ultrasonic Doppler Blood-Flow Sensing" IEEE Transactions on Sonics and Ultrasonics, Vol. SU-17, No. 3, July 1970, pp. 170–185. Each of the disclosed devices is essentially composed of a driver transmitting an ultrasonic wave signal toward and into a living body, a receiver receiving an echo signal of the transmitted ultrasonic wave signal, an oscillator generating an oscillation output signal having a pulse repetition frequency n times (n: an integer) as high as the repetition frequency of ultrasonic wave transmission, and a signal processing circuit processing the received echo signal. The method employed in the disclosed devices comprises transmitting the ultrasonic wave signal at the predetermined period toward a blood vessel in a living body, receiving an echo signal of the transmitted ultrasonic wave signal reflected by blood flow in the blood vessel, and measuring the Doppler shift frequency of the echo signal to measure the velocity and direction of blood flow in the blood vessel. By the above mentioned, the value of $v \cdot \cos\beta$ can be measured, where $\beta$ is the angle defined between the direction of blood flow and the direction of transmission of the ultrasonic wave signal, and v is the velocity of blood flow.

Figure 1:
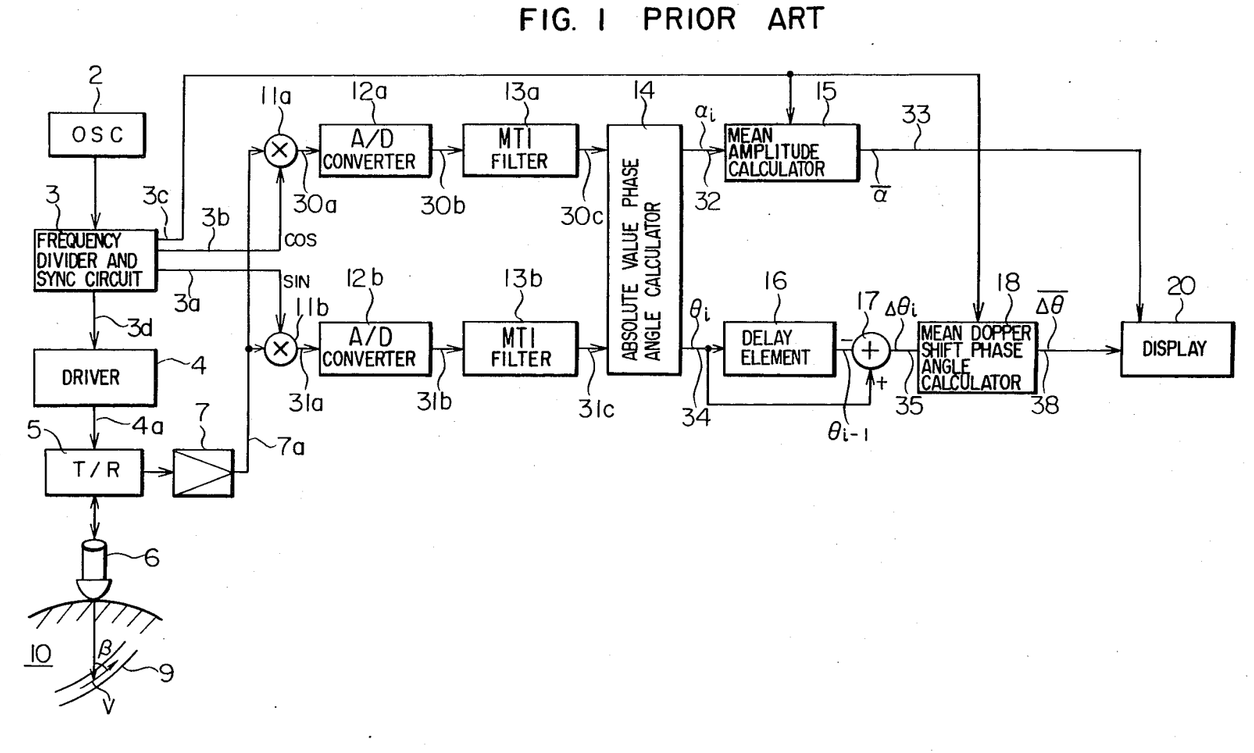
FIG. 1 is a block diagram of a prior art ultrasonic Doppler blood flow meter.

For the purpose of blood flow measurement in the manner described above, methods such as a zero-cross method and a fast Furrier transform (FET) method are commonly used. However, the latter method requires many hardware parts. with a view to decrease the number of hardware parts while taking into consideration the factors such as the accuracy of blood flow measurement, devices similar to a blood flow measuring device as shown in FIG. 1 are now proposed, as disclosed in, for example, JP-A-58-188433, JP-A-62-41645, JP-A-60-119929 and JP-A-61-25527. Referring to FIG. 1, a received input signal 7a is applied to quadrature detectors 11a and 11b. In the detector 11a, the input signal 7a is multiplied by a cosine wave signal 3b (described later) to provide an analog output signal 30a representing a real component ($R = \alpha \cos\theta$), while in the detector 11b, the input signal 7a is multiplied by a sine wave signal 3a (described later) to provide an analog output signal 31a representing an imaginary component ($I = \alpha \sin\theta$). These analog signals 30a and 31a are then A/D converted by A/D converters 12a and 12b respectively, and these digital signals representing the R and I components respectively are used to measure the Doppler shift phase angle thereby displaying the velocity v of blood flow on a display unit 20.

In the blood flow measuring device shown in FIG. 1, an oscillator 2 generates a stable high-frequency oscillation output signal which is applied to a frequency-dividing and synchronizing circuit 3. In response to the application of the high frequency signal, the circuit 3 generates a digital pulse signal 3d for ultrasonic pulse beam transmission, a sine wave signal 3a and a cosine wave signal 3b for quadrature detection, and a reset pulse signal 3c having a period n times (n: an integer) as large as that of the pulse signal 3d.

In response to the application of the digital pulse signal 3d, a driver circuit 4 applies an analog pulse signal 4a having, for example, a ½ cycle pulse to a probe 6 through a transmit/receive change-over circuit 5. The probe 6 is excited to transmit an ultrasonic pulse beam toward a blood vessel 9 of a living body 10 to be examined.

Figure 2:
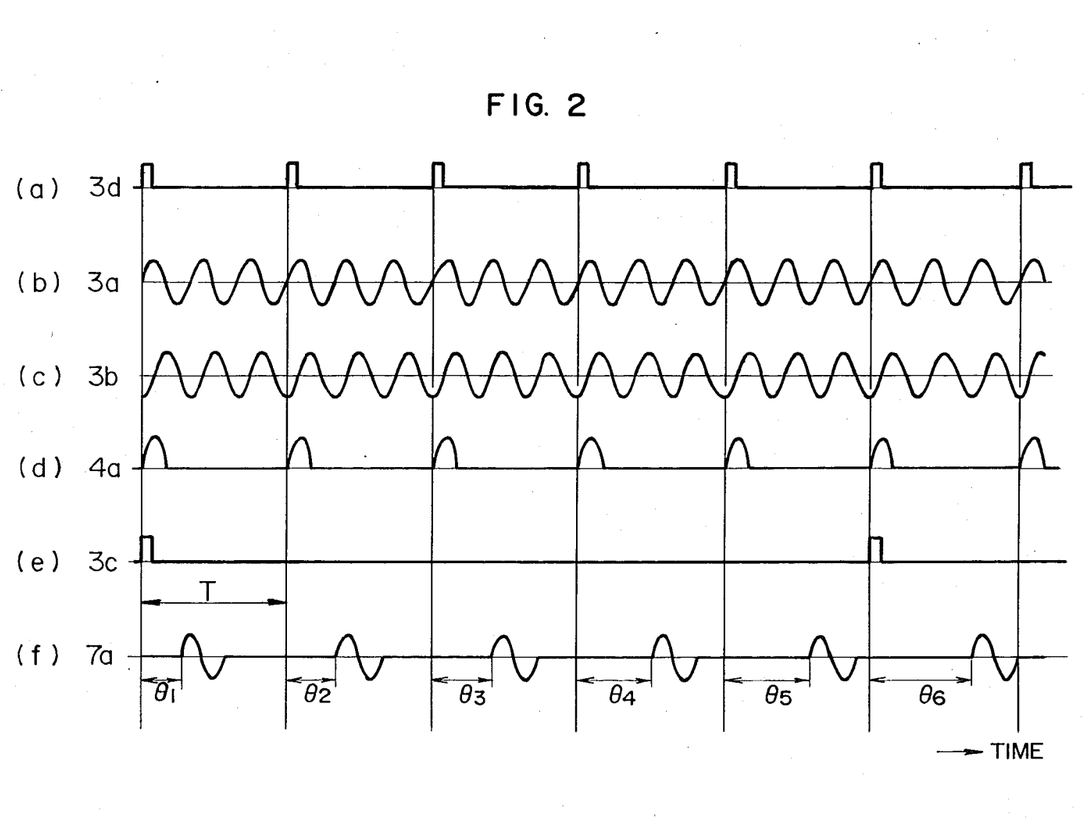
FIG. 2 shows signal waveforms appearing at various parts of FIG. 1.

The signal reflected from the blood vessel 9 of the living body 10 is converted by the probe 6 into an electrical signal, and this electrical signal is applied through the transmit/receive change-over circuit 5 to a high frequency amplifier 7 to be amplified and appears as a receive input signal 7a which is applied to the quadrature detectors 11a and 11b. FIG. 2 shows waveforms of the signals 3a, 3b, 3c, 3d, 4a and 7a shown in FIG. 1. The received input signal 7a having a waveform as shown in (f) of FIG. 2 is applied to the qudrature detectors 11a and 11b which are in the form of multipliers. In the detectors 11a and 11b, the receive input signal 7a is multiplied by the cosine and sine wave signals 3b and 3a having waveforms as shown in (c) and (b) of FIG. 2 to appear as the analog output signals 30a and 31a representing the R and I components respectively.

These analog signals 30a and 31a are then converted into digital signals 30b and 31b by the A/D converters 12a and 12b respectively, and these digital signals 30b and 31b are passed through MTI (moving target indication) filters 13a and 13b to appear as signals 30c and 31c respectively. These signals 30c and 31c are then applied to an amplitude and phase angle calculator 14, and an output signal 32 representing the amplitude $\alpha_i$ and an output signal 34 representing the phase angle $\theta_i$ are generated from the calculator 14. On the basis of the phase angle $\theta_i$ shown in (f) of FIG. 2, the Doppler shift phase angle $\Delta\theta_i(\Delta\theta_i = \theta_i - \theta_{i-1})$ is calculated, and, in order to improve the S/N ratio, the mean value $\overline{\Delta\theta}$ of a plurality of such Doppler shift phase angles is calculated by a mean Doppler shift phase-angle calculator 18. That is, the signal 34 representing the phase angle $\theta_i$ is applied, on one hand, directly and, on the other hand, through a delay element 16, to a subtractor 17. The delay element 16 has a delay time corresponding to one period T of the pulse signal 4a. Therefore, the subtactor 17 generates an output signal 35 representing the difference $\Delta\theta_i(\Delta\theta_i = \theta_i - \theta_{i-1})$ between the present phase angle $\theta_i$ and the preceding phase angle $\theta_{i-1}$, and such a signal 35 is applied to the mean Doppler shift phase-angle calculator 18. The calculator 18 calculates the mean value $\overline{\Delta\theta}(\overline{\Delta\theta} = (\Sigma(\theta_i - \theta_{i-1})/n)$ of n consecutive Doppler shift phase angles $\Delta\theta_i$, and its output signal 38 representing $\overline{\Delta\theta}$ is applied to the display 20. Thus, when the value of n is, for example, four, the reset pulse signal 3c having a waveform as shown in (e) of FIG. 2 has a period which is five times as large as that of the pulse signal 4a having a waveform as shown in (d) of FIG. 2. On the other hand, the signal 32 representing the amplitude $\alpha_i$ is applied to a mean amplitude calculator 15. The calculator 15 calculates the mean value $\overline{\alpha}(\overline{\alpha} = \Sigma\alpha_i/n)$ of n consecutive amplitude values $\alpha_i$, and its output signal 33 representing $\overline{\alpha}$ is applied to the display 20.

In the display 20, the mean value of Doppler shift phase angle $\overline{\Delta\theta}$ or the mean value of amplitude $\overline{\alpha}$ is displayed independently. The former relates the velocity, so does the latter the power of blood flow.

Figure 3A:
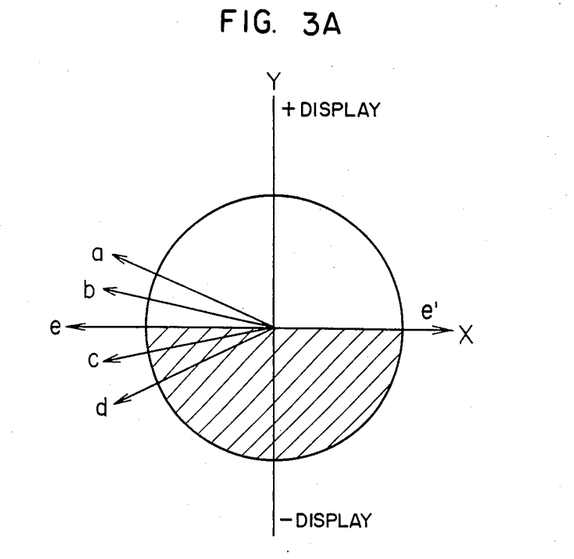
FIGS. 3A and 3B illustrate how a mean Doppler shift phase angle is calculated in the prior art Doppler blood flow meter shown in FIG. 1.
Figure 3B:
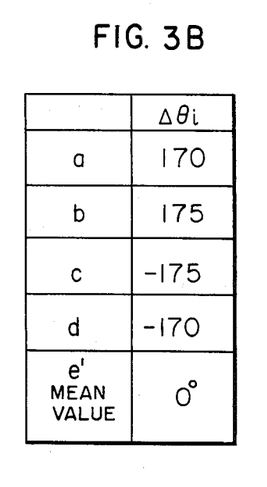

The prior art, blood flow measuring device shown in FIG. 1 has had such a problem that, in the calculation of the mean Doppler shift frequency, that is, the mean Doppler shift phase angle, the direction of the mean Doppler shift phase angle is not always the same as the direction of the Doppler shift phase angle as shown in FIG. 3A. This is because the Doppler shift phase angle that can be displayed is limited to within the range of $-\pi$ to $+\pi$ due to the structural limitation of the circuit. Therefore, the mean Doppler shift phase angle cannot be determined by merely simply calculating the numerical values of the Doppler shift phase angles. When, for example, the input signal 35 that is sequentially applied to the mean Doppler shift phase angle calculator 18, is successively representative of 170°, 175+, −175° and −170° as shown by the arrows a, b, c and d in FIG. 3A, mere addition of these numerical values and division of the sum by the factor of four does not provide a mean Doppler shift phase angle of 180° as shown by the arrow e in FIG. 3A, but provides a mean Doppler phase shift angle of 0° as shown by the arrow e' in FIG. 3A. FIG. 3B illustrates that the mean value shown by e' is 0 degrees.

The above problem is attributable to the fact that the displayable range of the Doppler shift phase angle is limited so as to simplify the hardware design for the purpose of minimizing the scale of the circuit.

SUMMARY OF THE INVENTION

With a view to obviate the defects of the prior art ultrasonic Doppler blood flow meter, it is an object of the present invention to provide an ultrasonic Doppler blood flow meter according to which the proper direction of Doppler shift phase angles can be measured when their mean value shows primarily an anlge close to 180° even if the displayable range of the phse angles is limited due to a structural limitation of hardware parts.

In the present invention which attains the above object, Doppler shift phase angles $\Delta\theta_i(=\theta_i-\theta_{i-1})$ are each resolved into two axial components on an orthogonal coordinate system, that is, an X-axis component (cos $\Delta\theta_i$) and a Y-axis component (sin $\Delta\theta_i$), and, after calculation of the mean value $\overline{X}=(\Sigma \cos \Delta\theta_i)/n$ of n consecutive X-axis components and the mean value $\overline{Y}=(\Sigma \sin \Delta\theta_i)/n$ of n consecutive Y-axis components, the mean Doppler shift phase angle $\overline{\Delta\theta}=\tan^{-1}(\overline{Y}/\overline{X})$ is calculated on the basis of these mean values $\overline{X}$ and $\overline{Y}$.

According to the ultrasonic Doppler blood flow meter of the present invention, the accuracy of calculation can be greatly improved without appreciably increasing the circuit scale as compared to that of the prior art blood flow meter.

DESCRIPTION OF THE PREFERRED EMBODIMENTS

Preferred embodiments of the present invention will now be described in detail with reference to the accompanying drawings.

Figure 3C:
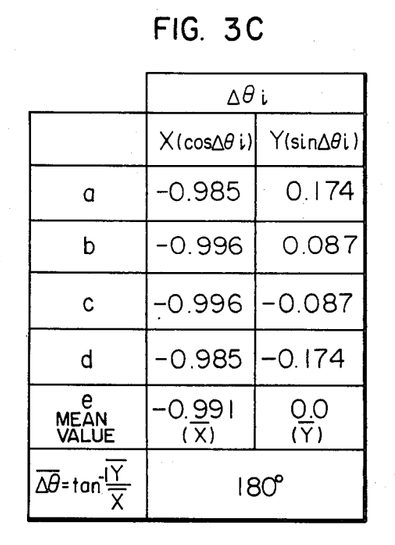
FIG. 3C illustrates how a mean Doppler shift phase angle is calculated according to the present invention.

In the present invention, Doppler shift phase angles $\Delta\theta_i=(\theta_i-\theta_{i-1})$ are each resolved into two axial components on an orthogonal coordinate system, that is, an X-axis component (cos $\Delta\theta_i$) and a Y-axis component (sin $\Delta\theta_i$) as shown in FIG. 3C, and the mean value $\overline{X}=(\Sigma \cos \Delta\theta_i)/n$ of n consecutive X axis components and the mean value $\overline{Y}=(\Sigma \sin \Delta\theta_i)/n$ of n consecutive Y-axis components are calculated to calculate the mean Doppler shift phase angle $\Delta\theta=\tan^{-1}(\overline{Y}/\overline{X})$ on the basis of these mean values $\overline{X}$ and $\overline{Y}$. Therefore, the mean Doppler shift phase angle $\Delta\theta$ can be detected with high accuracy irrespective of the values of the Doppler shift phase angles.

Figure 4:
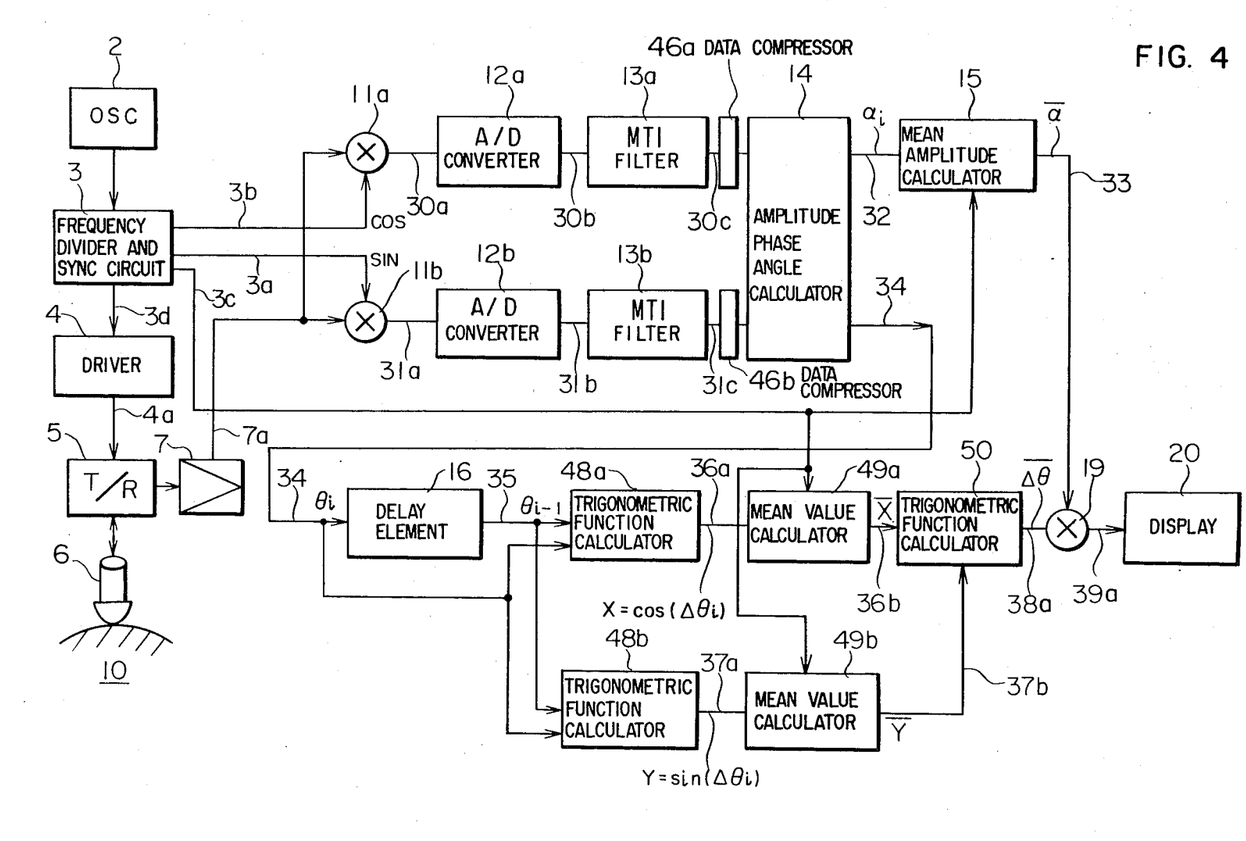
FIG. 4 is a block diagram of a preferred embodiment of the ultrasonic Doppler blood flow meter of the present invention.

FIG. 4 is a block diagram of a preferred embodiment of the ultrasonic Doppler blood flow meter according to the present invention, and, in FIG. 4, the same reference numerals are used to designate the same or equivalent functional parts appearing in FIG. 1.

The amplitude and phase angle calculator 14 in the embodiment of the present invention preferably includes a read-only memory (ROM), and, in response to the application of the signals 30c and 31c representing the real component (R=$\alpha \cos \theta$) and imaginary component (I=$\alpha \sin \theta$) from the MTI filters 13a and 13b respectively, the calculator 14 generates the signals 32 and 34 representing the amplitude $\alpha$ and the phase angle $\theta$ $$\left(\theta = \tan^{-1}\frac{I}{R} = \tan^{-1}\frac{\alpha \sin \theta}{\alpha \cos \theta}\right)$$

respectively. Therefore, the ROM included in the calculator 14 preferably stores a two-dimensional map of values of $\tan^{-1} I/R$ corresponding to the values of the two input signals 30c and 31c representing the R and I components respectively.

Figure 5:
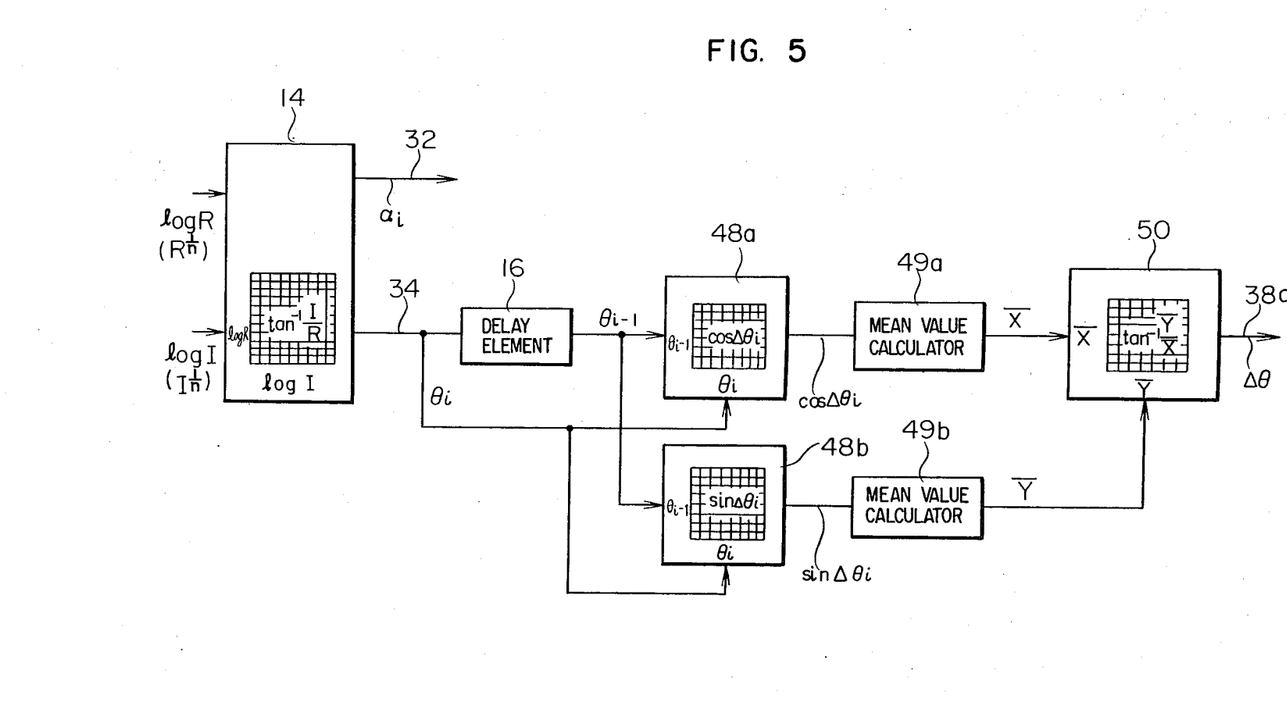
FIG. 5 shows in detail the arrangement of principal parts of the blood flow meter shown in FIG. 4.

The value of the phase angle $\theta_i$ represented by the output signal 34 of the calculator 14 lies generally in the range of 0 to $2\pi$ or $-\pi$ to $+\pi$. The output signal 34 of the calculator 14 representing the phase angle $\theta_i$ and the output signal 35 of the delay element 16 representing the preceding phase angle $\theta_{i-1}$ are applied to a pair of trigonometric function calculator 48a and 48b. Each of these trigonometric function calculators 48a and 48b acts to resolve the Doppler shift phase angle $\Delta\theta_i$ into its X-axis component and Y-axis component and preferably includes a read-only memory (ROM) such as that of Type 27512 made by the INTEL Corporation. The ROM in the calculator 48a preferably stores a two-dimensional map of values of cos $(\theta_i-\theta_{i-1})$ corresponding to the values of the two input signals 34 and 35 representing the phase angles $\theta_i$ and $\theta_{i-1}$ respectively, as shown in FIG. 5. Therefore, the calculator 48a generates an output signal 36a representing the value of cos $(\theta_i - \theta_{i-1})(= \cos \Delta\theta i)$ corresponding to the values of the phase angles $\theta_i$ and $\theta_{i-1}$ applied as the inputs.

Similarly, the calculator 48b preferably includes a ROM which stores a two-dimensional map of values of sin $(\theta_i - \theta_{i-1})$ corresponding to the values of the two input signals 34 and 35 representing the phase angles $\theta_i$ and $\theta_{i-1}$ respectively and generates an output signal 37a representing the value of sin $(\theta_i - \theta_{i-1})(= \sin \Delta\theta_i)$ corresponding to the values of the phase angles $\theta_i$ and $\theta_{i-1}$ applied as the inputs. The output signals 36a and 37a of the calculators 48a and 48b are applied to mean value calculators 49a and 49b respectively.

The pulse signal 3c, whose period is n times (for example, five times) as large as that of the pulse signal 4a, is applied to these calculators 49a and 49b. Therefore, the calculator 49a calculates the mean value $$\overline{X}\left( = \frac{\sum\limits_{i=2}^{i=5} \cos(\theta_i - \theta_{i-1})}{4} \right)$$

of X-axis components cos $\Delta\theta_i$ of five consecutive Doppler shift phase angles $\Delta\theta_i$ and generates an output signal 36b representing the mean value $\overline{X}$. Similarly, the calculator 49b calculates the mean value $$\overline{Y}\left( = \frac{\sum\limits_{i=2}^{i=5} \sin(\theta_i - \theta_{i-1})}{4} \right)$$

of Y-axis components sin $\Delta\theta_i$ of five consecutive Doppler shift phase angles $\Delta\theta_i$ and generates an output signal 37b representing the mean value $\overline{Y}$. Thereafter, the calculators 49a and 49b are reset by the reset pulse signal 3c to start to calculate the mean values of succeeding five consecutive X-axis components and five consecutive Y-axis components respectively.

The output signals 36b and 37b of the respective calculators 49a and 49b are applied to a trigonometric function calculator 50 which calculates the mean Doppler shift phase angle $\overline{\Delta\theta}(=\tan^{-1}(\overline{Y}/\overline{X}))$ on the basis of the mean values $\overline{X}$ and $\overline{Y}$.

The calculator 50 preferably includes a read-only memory (ROM) such as that of Type 27512 made by the INTEL Corporation. This ROM stores a two-dimensional map of values of $\tan^{-1}(\overline{Y}/\overline{X})$ corresponding to the values of the mean phase angles $\overline{X}$ and $\overline{Y}$ applied as the inputs. Therefore, the calculator 50 generates an output signal 38a representing the value of $\tan^{-1}(\overline{Y}/\overline{X})$ corresponding to the input values of $\overline{X}$ and $\overline{Y}$. Because the calculation of the value of $\tan^{-1}(\overline{Y}/\overline{X})$ is based on a two-dimensional map stored in a ROM, the values of $\overline{\Delta\theta}$ are determined on the basis of the polarities of $\overline{X}$ and $\overline{Y}$ as follows:
where:

$\overline{X}=0, \overline{Y}=0$ then $\overline{\Delta\theta}=0°$ $\overline{X}>0, \overline{Y}>0$ then $0°<\overline{\Delta\theta}<90°$ $\overline{X}>0, \overline{Y}<0$ then $0°>\overline{\Delta\theta}>-90°$ $\overline{X}<0, \overline{Y}>0$ then $90°<\overline{\Delta\theta}<180°$ $\overline{X}<0, \overline{Y}<0$ then $-90°>\overline{\Delta\theta}>-180°$ By use of a two dimensional map, discrimination between values in the first and third quadrants and in the second and fourth quadrants is easily ascertained.

On the other hand, the output signal 32 of the amplitude and phase angle calculator 14 representing the amplitude $\alpha_i$ is applied to the mean amplitude calculator 15. The pulse signal 3c is also applied to this calculator 15. The calculator 15 calculates the mean value $$\overline{\alpha} = \left( \frac{\sum\limits_{i=2}^{i=5} \alpha_i}{4} \right)$$

of five consecutive amplitude values $\alpha_i$ and generates the output signal 33 representing the mean amplitude $\overline{\alpha}$.

The signal 38a representing $\overline{\Delta\theta}$ is multiplied by the signal 33 representing $\overline{\alpha}$ by the multiplier 19 so as to weight the mean Doppler shift phase angle $\overline{\Delta\theta}$ by the mean amplitude $\overline{\alpha}$, and an output signal 39a representing the result of multiplication $\overline{\alpha} \cdot \overline{\Delta\theta}$ is applied to the display unit 20 to display the multiplication value of the velocity v and the amplitude $\alpha$ of blood flow.

It is possible to display the mean value of Doppler shift phase angle $\overline{\Delta\theta}$ or the mean value of amplitude $\overline{\alpha}$ independently as the same as the prior art as shown in FIG. 1.

Therefore, in the first embodiment of the present invention, phase angles as shown by the arrows a to d in FIG. 3A are resolved into two axial components as shown in FIG. 3C, and their mean values $\overline{X}$ and $\overline{Y}$ are calculated respectively, so that the correct mean Doppler shift phase angle $\overline{\Delta\theta}$ can be detected with high accuracy.

It is commonly done to limit the displayable range of data, that is, to decrease the displayed number of bits of data in order to reduce the circuit scale (the number of circuit elements). In the case of the embodiment shown in FIG. 4, the input signal 7a is multiplied by the cosine wave signal and the sine wave signal, and the resultant analog signals are applied, after A/D conversion, to the MTI filters 13a and 13b respectively. Output data of these MTI filters 13a and 13b may possibly require a number of bits larger than that of output data of the other parts of the circuit from the aspect of accuracy. When the number of bits of the input signal 7a is, for example, 7, the output signals 30c and 31c of the respective MTI filters 13a and 13b may require 12 bits. In this case, when the 12-bit output data of the MTI filters 13a and 13b are applied intact to the amplitude and phase angle calculator 14, the calculator 14 will require a plurality of 8-bit ROM's, resulting in complexity of the circuit structure. To avoid such a structural complexity, data compressors 46a and 46b for compressing the 12-bit inputs into, for example, 8-bit inputs are preferably provided on the input side of the calculator 14. These data compressors 46a and 46b may be those which generate output signals representing logarithmic values log R and log I or n-th roots $R^{1/n}$ and $I^{1/n}$ of the input signals representing the R and I components respectively.

The 8-bit data output signals of the data compressors 46a and 46b are applied to the amplitude and phase angle calculator 14, and the phase-angle data output signal 34 of, for example, 12 bits is generated from the calculator 14.

In such a case, the ROM included in the calculator 14 stores preferably a two-dimensional map of output values of $\theta = \tan^{-1} I/R$ corresponding to the two input values of log R and log I (or $R^{1/n}$ and $I^{1/n}$) as shown in FIG. 5, and the resultant data output signal 34 of the calculator 14 represents $\theta_i$ of, for example, 12 bits.

The calculator data output signal 34 representing the phase angle $\theta_i$ of 12 bits is applied to the trigonometric function calculators 48a and 48b. In the calculators 48a and 48b, more significant 8 bits of the 12-bit data input signal representing $\theta_i$ are used for calculation. In this case, the trigonometric function calculator 50 generates a data output signal of 7 bits.

Therefore, provision of a single ROM in each of the amplitude and phase angle calculator 14 and trigonometric function calculators 48a, 48b, 50 is only required so that the circuit structure can be simplified.

The numbers of bits of data outputs of the individual circuit elements are referred to for illustrative purposes only, and the present invention is in no way limited to such specific numbers of bits of data outputs.

It can be seen from the above description that the embodiment is advantageous in that the hardware can be simplified, and the circuit scale can be reduced to a minimum.

Figures 6, 7:
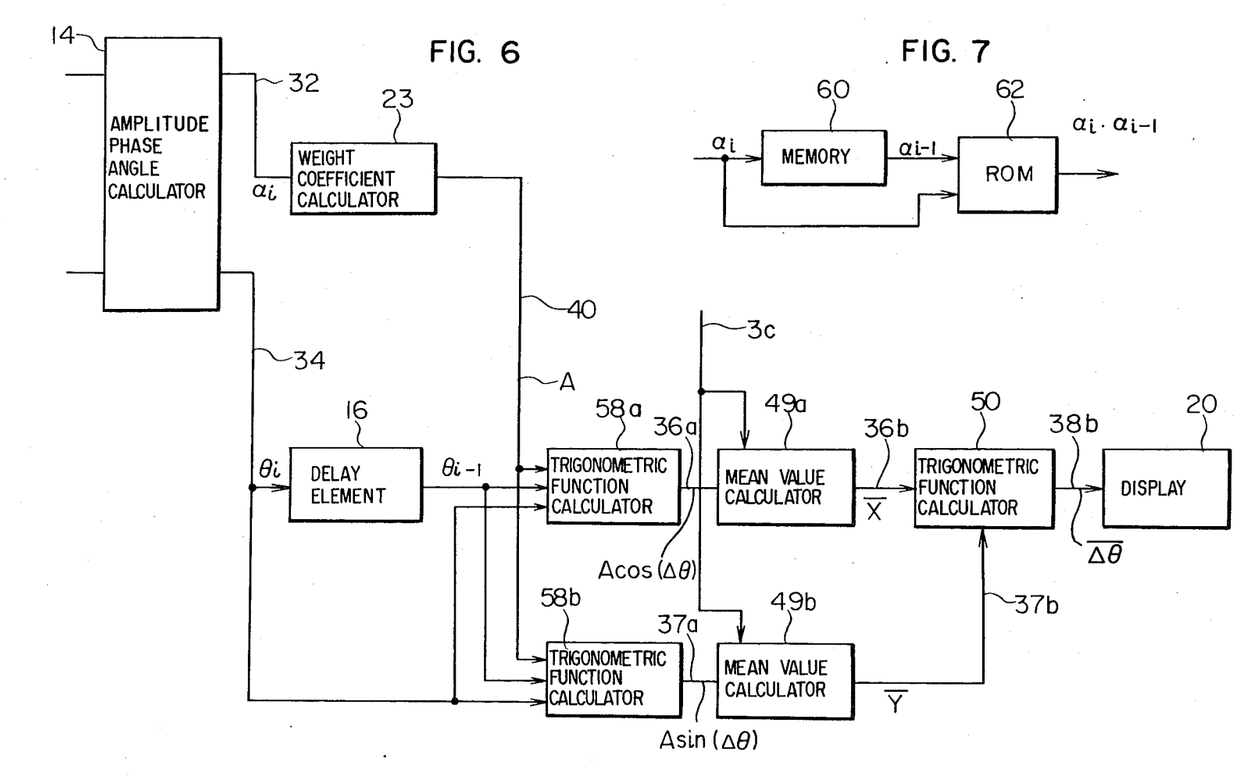
FIG. 6 is a block diagram of another preferred embodiment of the ultrasonic Doppler blood flow meter of the present invention.
FIG. 7 is a circuit diagram showing the structure of one form of the weighting coefficient calculator shown in FIG. 6.

FIG. 6 is a block diagram of a second embodiment of the ultrasonic Doppler blood flow meter according to the present invention, and, in FIG. 6, the same reference numerals are used to designate the same or equivalent functional parts included in the first embodiment.

In this second embodiment, a weighting coefficient corresponding to the amplitude $\alpha_i$ of the input signal 7a is used in the calculation of the mean Doppler shift phase angle $\overline{\Delta\theta}$. By the use of such a weighting coefficient, the mean Doppler shift phase angle $\overline{\Delta\theta}$ is determined in dependence on an input signal having a large amplitude and without dependence on an input signal having a small amplitude, so as to improve the accuracy of detection of the mean Doppler shift phase angle $\overline{\Delta\theta}$.

In the second embodiment shown in FIG. 6, a weighting coefficient $A_i$ corresponding to the amplitude $\alpha_i$ of the input signal 7a is used for weighting the X-axis component $\cos \Delta\theta_i$ and Y-axis component $\sin \Delta\theta_i$ of the Doppler shift phase angle $\Delta\theta_i$. For this purpose, a weighting coefficient calculator 23 is provided which receives the output signal 32 of the amplitude and phase angle calculator 14 as its input and generates an output signal 40 representing the value of $A_i$. This output signal 40 is applied to each of trigonometric function calculators 58a and 58b.

The weighting coefficient $A_i$ provided by the output signal 40 of the weighting coefficient calculator 23 is as follows:

$A_i = ((\alpha_i + \alpha_{i-1})/2)^2$ $A_i = \alpha_i \cdot \alpha_{i-1}$ $A_i = (\alpha_i \cdot \alpha_{i-1})^{\frac{1}{2}}$ $A_i = \alpha_i$ $A_i = \alpha_i^2$ $A_i = \alpha_i + \alpha_{i-1}$ $A_i = \log (\alpha_i \cdot \alpha_{i-1})$ In the above expressions, $\alpha_i$ and $\alpha_{i-1}$ designate a first and a second amplitude output respectively of the amplitude and phase angle calculator 14. FIG. 7 is a circuit diagram showing the structure of one form of the weighting coefficient calculator 23 from which the signal 40 representing, for example, the weighting coefficient $A_i = \alpha_i \cdot \alpha_{i-1}$ is generated. Referring to FIG. 7, a memory 60 acts as a delay element, and its output is $\alpha_{i-1}$ when its input is $\alpha_i$. A ROM 62 preferably stores a two-dimensional map of power values of $\alpha_i \cdot \alpha_{i-1}$ which is the product of its two amplitude inputs $\alpha_i$ and $\alpha_{i-1}$. The trigonometric function calculators 58a and 58b preferably include ROM's for generating $A_i \cdot \cos(\theta_i - \theta_{i-1})$ and $A_i \cdot \sin(\theta_i - \theta_{i-1})$ as their outputs respectively in response to the application of the three inputs representing $A_i$, $\theta_i$ and $\theta_{i-1}$. More precisely, the calculator 58a includes a ROM storing a three-dimensional map of values of $A_i \cdot \cos(\theta_i - \theta_{i-1})$ corresponding to its three inputs $A_i$, $\theta_i$ and $\theta_{i-1}$, and, similarly, the calculator 58b includes a ROM storing a three-dimensional map of values of $A_i \cdot \sin(\theta_i - \theta_{i-1})$ corresponding to its three inputs $A_i$, $\theta_i$ and $\theta_{i-1}$. The output signals 36a and 37a of the trigonometric function calculators 58a and 58b representing $A_i \cdot \cos(\theta_i - \theta_{i-1})$ and $A_i \cdot \sin(\theta_i - \theta_{i-1})$ are applied to the mean value calculators 49a and 49b respectively. The calculators 49a and 49b calculate the mean values $\overline{X}$ and $\overline{Y}$ of n continuous outputs $A_i \cdot \cos \Delta\theta_i$ and $A_i \cdot \sin \Delta\theta_i$ of the trigonometric function calculators 58a and 58b respectively. Thus, when n is, for example, five, the calculator 49a calculates the mean value $$\overline{X}\left(\overline{X} = \frac{\sum_{i=2}^{i=5} A_i \cos(\theta_i - \theta_{i-1})}{4}\right)$$

and generates its output signal 36b representing the mean value $\overline{X}$, and the calculator 49b calculates the mean value $$\overline{Y}\left(\overline{Y} = \frac{\sum_{i=2}^{i=5} A_i \sin(\theta_i - \theta_{i-1})}{4}\right)$$

and generates its output signal 37b representing the mean value $\overline{Y}$. The output signals 36b and 37b of the calculators 49a and 49b representing the mean values $\overline{X}$ and $\overline{Y}$ respectively are applied to the trigonometric function calculator 50, and, in the calculator 50, the weighted mean Dopper shift phase angle $\overline{\Delta\theta}(\overline{\Delta\theta} = \tan^{-1} \overline{Y}/\overline{X})$ is calculated on the basis of the mean values $\overline{X}$ and $\overline{Y}$. The output signal 38b of the calculator 50 is applied to the display unit 20 as the signal representing the velocity v of blood flow.

Thus, according to the present invention described above, Doppler shift phase angles $\Delta\theta_i = (\theta_i - \theta_{i-1})$ are resolved into two axial components on an orthogonal coordinate system, that is, X-axis components ($\cos \Delta\theta_i$) and Y-axis components ($\sin \Delta\theta_i$), and the mean value $\overline{X} = (\Sigma \cos \Delta\theta_i)/n$ of n consecutive X-axis components and the mean value $\overline{Y} = (\Sigma \sin \Delta\theta_i)$ of n consecutive Y-axis components are calculated to calculate the mean Doppler shift phase angle $\overline{\Delta\theta} = \tan^{-1}(\overline{Y}/\overline{X})$. Therefore, the mean Doppler shift phase angle can be detected with high accuracy without appreciably increasing the circuit scale, even when the displayable range is limited to within $-\pi$ to $+\pi$ due to the structural limitation of the hardware and also even when the mean Doppler shift phase angle has a value close to $\pi$.

We claim:

1. An ultrasonic Doppler blood flow meter comprising:

ultrasonic wave transmitting and receiving means for sequentially transmitting ultrasonic waves toward and into a living body at a predetermined time period and receiving their echo signals;

means to detect a real component and an imaginary component of each successive received echo signals in quadrature;

converting means for sequentially subjecting the real component and the imaginary component to circuitry for calculating a phase angle ($\Theta_i$) of a received echo signal relative to the transmitted ultrasonic wave;

two-axial-component resolving means for resolving the hase angle ($\Theta_i$) calculated by said converting means and its preceding phase angle ($\Theta_{i-1}$) directly into an X-axis component ($\cos \Delta\Theta_i$) and a Y-axis component ($\sin \Delta\Theta_i$) of the difference ($\Delta\Theta_i$) between the phase angle ($\Theta_i$) and its preceding phase angle ($\Theta_{i-1}$) on an orthogonal coordinate system;

means for calculating mean values ($\overline{X}, \overline{Y}$) of n consecutive X-axis components and n consecutive Y-axis components, n being a predetermined integer number, respectively detected by said two-axial-component resolving means when the ultrasonic wave is transmitting n consecutive times from said ultrasonic wave transmitted and receiving means;

mean Doppler shift phase-angle calculating means for obtaining as an output a mean Doppler shift phase-angle ($\Delta\Theta$), by distinguishing to which quadrant among four quadrants the obtained angle ($\Delta\Theta$) belongs, utilizing signals corresponding to said mean values ($\overline{X}, \overline{Y}$) of the X-axis and Y-axis components by taking into consideration polarities of each of the mean values ($\overline{X}, \overline{Y}$) according to the equation $\Delta\Theta = \tan^{-1}(\overline{Y}/\overline{X})$; and display means operatively connected to the output of said mean Doppler shift phase-angle calculating means for displaying velocity of blood flow.

2. An ultrasonic Doppler blood flow meter according to claim 1, wherein said mean Doppler shift phase-angle calculating means includes a read-only memory having a two-dimensional map which stores values of $\tan^{-1}(\overline{X}/\overline{Y})$ with respect to positive and negative values of the X-axis and Y-axis components.

3. An ultrasonic Doppler blood flow meter according to claim 1, wherein data compressing means for compressing said real component and said imaginary component respectively are provided on an input side of said converting means.

4. An ultrasonic Doppler blood flow meter according to claim 1, wherein said converting means sequentially calculates amplitude of the echo signal from said real and imaginary components, and said ultrasonic Doppler blood flow meter further comprises means for calculating a mean value of n consecutive amplitude values calculated by said converting means when the ultrasonic wave is transmitted n consecutive times from said ultrasonic wave transmitting and receiving means, and means multiplying said mean Doppler shift phase angle by the mean value of the n consecutive amplitude values for displaying the product representing the velocity of blood flow of said display unit.

5. An ultrasonic Doppler blood flow meter according to claim 1, wherein said converting means sequentially calculates the amplitude of the echo signal from said real and imaginary components, and said ultrasonic Doppler blood flow meter further comprises weighting means for weighting the X-axis and Y-axis components generated from said two-axial-component resolving means by a weighting coefficient relating to the amplitude calculated by said converting means.

6. In an ultrasonic Doppler blood flow meter including ultrasonic wave transmitting and receiving means for sequentially transmitting an ultrasonic wave toward and into a living body at a predetermined period and receiving its echo signal;

means for sequentially subjecting the echo signal to quadrature detection to detect a real component (R) and an imaginary component (I) of the received echo signal;

converting means for sequentially subjecting the real component and the imaginary component to calculate a phase angle ($\Theta i$) of the received echo signal relative to the transmitted ultrasonic wave;

two-axial-component resolving means for resolving the phase angle ($\Theta i$) calculated by said converting means and its preceding one ($\Theta i - 1$) into a real component (R) and an imaginary component (I) of the difference ($\Delta\Theta i$) between the phase angle ($\Theta i$) and its preceding phase angle ($\Theta i -1$); and means for calculating mean values ($\overline{R}, \overline{I}$) of the real and imaginary components, the improvement comprising:

mean Doppler shift phase-angle calculating means for obtaining the mean Doppler phase shift-angle ($\overline{\Delta\Theta}$), by distinguishing to which quadrant among four quadrants the obtained angle ($\overline{\Delta\Theta}$) belongs, on the basis of the mean values ($\overline{R}, \overline{I}$) of the real and imaginary components by taking into consideration polarities of each of the mean values ($\overline{R}, \overline{I}$) according to an equation $\Delta\Theta = \tan^{-1}(\overline{I}, \overline{R})$; and display mans operatively connected to the output of said mean Doppler shift phase-angle calculating means for displaying the velocity of blood flow.

* * * * *